United States Patent [19]

Kuroha

[11] 4,105,338
[45] Aug. 8, 1978

[54] REFLECTION TYPE ELLIPSOMETER FOR MEASURING THIN FILM PHASE DIFFERENCE AND THICKNESS

[75] Inventor: Noboru Kuroha, Yokohama, Japan

[73] Assignee: Nippon Kogaku K.K., Tokyo, Japan

[21] Appl. No.: 679,689

[22] Filed: Apr. 23, 1976

[30] Foreign Application Priority Data

May 2, 1975 [JP] Japan .................................. 50-52539

[51] Int. Cl.² .............................................. G01J 4/00
[52] U.S. Cl. ................................................... 356/118
[58] Field of Search ............................. 356/114–119, 356/33–35; 250/225; 350/150

[56] References Cited

U.S. PATENT DOCUMENTS

| | | | |
|---|---|---|---|
| 1,978,434 | 10/1934 | Maris | 356/115 |
| 3,602,597 | 8/1971 | Sproul | 356/117 |

FOREIGN PATENT DOCUMENTS

320,503 12/1902 France ..................................... 356/116

*Primary Examiner*—John K. Corbin
*Assistant Examiner*—Wm. H. Punter
*Attorney, Agent, or Firm*—Shapiro and Shapiro

[57] ABSTRACT

A reflection type ellipsometer for measuring the phase difference of a sample, which comprises a light source, a polarizer, a sample, an analyzer and a photoelectric converter element arranged in the conventional manner. In accordance with the present invention the ellipsometer includes an adjustable phase difference compensating plate which is disposed on the light path between the polarizer and the analyzer and at an azimuth of 0° with respect to the sample surface, the phase difference ($\Delta c$) introduced by the compensating plate being preset to a value which eliminates a predetermined or reference phase difference ($\Delta o$). The ellipsometer of the present invention further includes a double-refractive element which introduces a double refraction phase difference proportional to a voltage applied thereto. The double-refractive element is also disposed on the light path between the polarizer and the analyzer. Control means is provided for comparing the output voltage from a photoelectric converter element with a predetermined or reference voltage and for applying to the double-refractive element a voltage which causes the double-refractive element to introduce a phase difference ($\Delta k$) which eliminates the phase difference ($\Delta s$) corresponding to the deviation of the phase difference ($\Delta o + \Delta s$) of the sample from the predetermined phase difference ($\Delta o$).

7 Claims, 7 Drawing Figures

REFLECTION TYPE ELLIPSOMETER FOR MEASURING THIN FILM PHASE DIFFERENCE AND THICKNESS

BACKGROUND OF THE INVENTION

1. Field of the Invention

This invention relates to a device for rapidly measuring the thickness of thin film deposited on the surface of a body by monitoring polarized light reflected from the surface of the body.

2. Description of the Prior Art

Ellipsometers have heretofore been used to analyse the surface of a body or thin film thereon. Most ellipsometers include a movable portion for mechanically rotating or sliding a polarizing plate or a phase plate. This approach has drawbacks, principally in that rapid measurement is difficult and inconvenient to achieve, particularly during so-called on-line measurement in which the thin film on a body is analysed in the course of a manufacturing process.

SUMMARY OF THE INVENTION

This invention provides an ellipsometer by means of which analysis of the surface of a body or of a thin film on a body is achieved under electrical control and without using any movable portion.

According to the present invention, a reflection type ellipsometer for measuring the phase difference possessed by a sample comprises a light source emitting monochromatic light of a particular wavelength; a polarizer for linearly polarizing the light from the light source and having the azimuth thereof disposed at −45° or +45° with respect to the incidence surface (reference surface) of the sample, the sample being disposed at a position for reflecting the linearly polarized light from the polarizer; an analyser disposed on the path of reflected light from the sample and at an azimuth angle of +45° of −45° with respect to the incidence surface or the sample; an adjustable phase difference compensating plate which is disposed on the light path between the polarizer and the analyser and at an azimuth angle of 0° with respect to the reference surface, the phase difference introduced by the compensating plate being preset to a value which eliminates a predetermined or reference phase difference; a double-refractive element for producing a double-refraction phase difference proportional to a voltage applied thereto; a photoelectric converter element for photoelectrically converting the output light from the analyser; and control means for comparing the output voltage from the photoelectric converter element with a predetermined or reference voltage and for applying to the double-refractive element a voltage which causes the double-refractive element to introduce a phase difference corresponding to the amount of deviation of the phase difference of the sample from the predetermined or reference phase difference.

The phase difference compensating plate and the double-refractive element may be disposed at any desired positions between the polarizer and the analyser. Thus, for example, the phase difference compensating plate may be disposed on the light path between the polarizer and the sample, and the double-refractive element may be disposed on the light path between the sample and the analyser. Alternatively, the double-refractive element may be disposed on the light path between the polarizer and the sample, and the phase difference compensating plate may be disposed on the light path between the sample and the analyser. As a further alternative, the phase difference compensating plate and the double-refractive element may be disposed on the light path between the polarizer and the sample. Still alternatively, the phase difference compensating plate and the double-refractive element may be disposed on the light path between the sample and the analyser. The ellipsometer may further comprise means for indicating the value of the voltage applied to the double-refractive element by the control means.

The invention is more fully apparent from the following detailed description thereof taken in conjunction with the accompanying drawings.

DESCRIPTION OF THE PREFERRED EMBODIMENTS

Assume that a predetermined or reference phase difference desired of a sample is $\Delta o$, that the actual phase difference of the sample is measured to be $\Delta o + \Delta s$, so that $\Delta s$ is the deviation or error phase difference, that the phase difference resulting from a double-refractive plate such as KDP is $\Delta k$, and that the phase difference resulting from a phase plate is $\Delta c$. If a compensation method (null method) is used, then when the sum of all the phase differences, $\Delta$, becomes 0, the quantity of light entering a light sensing element is 0. This can be formulated as follows:

$$\Delta = \Delta o + \Delta s + \Delta k + \Delta c = 0,$$

where $\Delta o$ is a reference phase difference such as the average value of the phase differences of samples to be measured and may correspond to a set or control value during a manufacturing process and to a reference value during inspection of products. $\Delta s$, then, represents an amount of variation or deviation from the set value or the reference value.

The foregoing equation may be transformed into:

$$\Delta o + \Delta s = -(\Delta k + \Delta c)$$

Thus, the phase difference of the sample may be given by $\Delta k + \Delta c$. The above equation may in turn be transformed into:

$$(\Delta o + \Delta c) + (\Delta s + \Delta k) = 0$$

Figure 1:
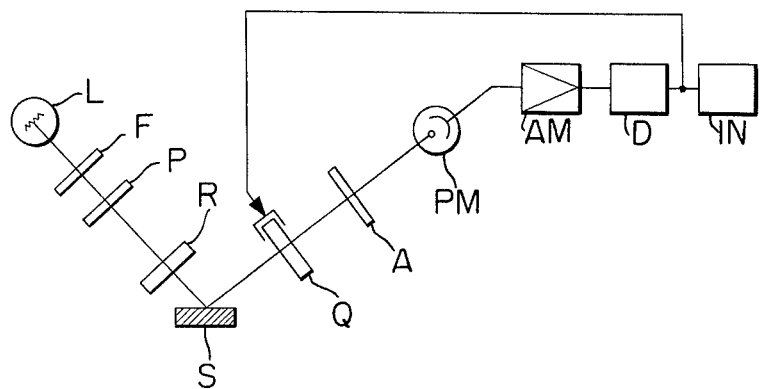
FIG. 1 is a schematic view showing an embodiment of the present invention.

In order that this equation may be satisfied, there should be these relations: $\Delta o + \Delta c = 0$ and $\Delta s + \Delta k = 0$. In other words, the phase difference $\Delta o$ of the sample, as the set value or the reference value, should first be compensated for by the phase difference of a phase plate, and then the amount of deviation $\Delta s$ should be compensated for by the phase difference of the double-refractive plate such as KDP. FIG. 1 shows an embodiment of the present invention which satisfies the above-described conditions.

Figure 2:
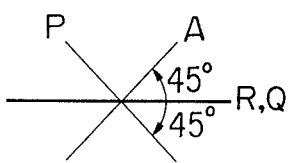
FIGS. 2 and 3 A. & B. explain details of the embodiment of the present invention.

In FIG. 1, light from a light source L is transformed into light of a particular wavelength by an interference filter F. Represented by P is a polarizer which, as illustrated in FIG. 2, is disposed at an azimuth of −45° with respect to the incidence surface (the angles hereinafter mentioned refer to the azimuth angles of respective elements disposed with respect to the incidence surface as the reference). R designates an adjustable phase plate such as Soleil-Barinet's compensator disposed at 0°. S designates a sample also disposed at 0°. Q is a double-refractive substance such as KDP, disposed at 0°. KDP, as is well known, is a uniaxial crystal cut perpendicularly to the Z-axis thereof, and if a voltage is applied thereto, the KDP acts as a biaxial crystal which creates a double-refraction phase difference proportional to the voltage applied. Designated by A is an analyser which, as depicted in FIG. 2, is disposed at an aximuth angle of 45°. PM is a light-sensing element such as photomultiplier. Designated by AM is an amplifier for amplifying the output of the light-sensing element, and D is a detector. The detector D serves to compare, with a reference voltage, for example, 0 volts, the output from the light-sensing element PM which senses the light passed through the analyser A, and to apply to the KDP a voltage for nullifying the quantity of light entering the light-sensing element PM. The output of the amplifier AM is connected to the input of the detector D, and the output of detector D is connected to the KDP and to a recording meter IN.

Figure 3A:
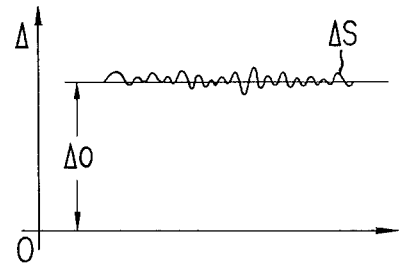
Figure 3B:
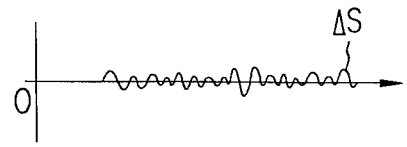

In the above-described construction of an embodiment of the present invention, the monochromatic light passed through the interference filter F is transformed by the polarizer P into linearly polarized light having an azimuth angle of −45°. Phase plate R introduces to this linearly polarized light a phase difference $\Delta c$, which is equal to the set value or the reference value $\Delta o$ desired of the sample, and thus phase plate R provides elliptically polarized light corresponding to that phase difference. The light is then reflected by the sample S and undergoes the phase variation $\Delta o + \Delta s$ actually introduced by the sample. This phase variation $\Delta o + \Delta s$ is illustrated in FIG. 3A. The phase difference $\Delta o$, which is the set value or the reference value of the sample, is eliminated by virtue of the phase variation $\Delta c$ introduced by the phase plate R (since $\Delta o + \Delta c = 0$) but the phase difference $\Delta s$, representing the amount of variation from the set value or the reference value, is not compensated for and so still is present, as illustrated in FIG. 3B. Such light passes through the KDP, which initially has 0 volts applied thereto, and further through the analyser A to the light-sensing element PM, which senses the light. Since the quantity of light from the analyser A is in proportion to $\sin^2(\Delta s/2)$, the output from the light-sensing element PM is likewise in proportion to $\sin^2(\Delta s/2)$. This output is amplified by the amplifier AM and enters the detector D. The output of the detector D provides a voltage which is used to nullify the quantity of light entering the light-sensing element PM. This output is recorded by the recording meter IN while, at the same time, it is applied to the KDP. Upon application of such voltage thereto, the KDP introduces a phase difference $\Delta k$ which compensates for the phase difference $\Delta s$ of the light which is then passing therethrough; i.e., the light from the KDP is made into completely linearly polarized light whose direction of vibration is orthogonal to the direction of vibration of the analyser A. Thus, $\Delta s + \Delta k = 0$, and the phase difference of the entire system is $(\Delta o + \Delta c) + (\Delta s + \Delta k) = 0$. From this relation, the phase difference $\Delta o + \Delta s$ of the sample may be obtained as $-(\Delta c + \Delta k)$.

If a different sample is to be measured, the phase difference $\Delta c$ which is the set value or the reference value necessarily becomes different, but measurement can be carried out without any inconvenience by adjusting the phase plate R to that value prior to the measurement.

Figure 4A:
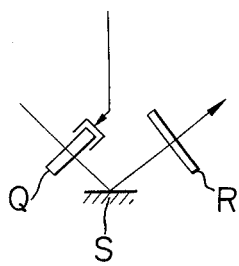
FIGS. 4 A, B, C, illustrate alternative embodiments of the present invention.
Figure 4B:
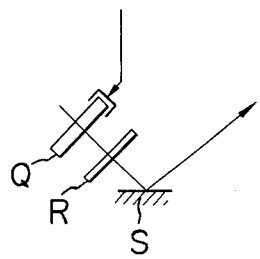
Figure 4C:
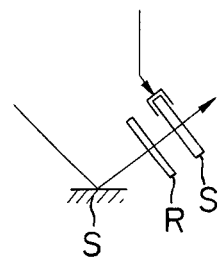

FIG. 4 shows another embodiment of the present invention. In the embodiment previously described with reference to FIG. 1, the adjustable phase plate R, the sample and the KDP are arranged in the named order, whereas any desired order of arrangement may be adopted between the polarizer P and the analyser A. Thus as illustrated in FIG. 4A, the double-refractive substance Q, which may be KDP, may be between the polarizer and the sample, while the variable phase plate R is between the sample and the analyser. Likewise, as shown in FIG. 4B, the double-refractive substance Q and the adjustable phase plate R may both be between the polarizer and the sample. Similarly, as illustrated in FIG. 4C, the double-refractive substance Q and the adjustable phase plate R may both be between the sample and the analyser.

Further, in the embodiment of FIG. 1, the polarizer is disposed at an azimuth of −45° with respect to the incidence surface and the analyser is disposed at an azimuth of +45° with respect to the incidence surface, but this relationship may be inverted. In other words, the polarizer may be at the azimuth of +45° and the analyser at the azimuth of −45°, both with respect to the incidence surface.

According to the present invention, as has been described above, no mechanically movable portion is required, and this enables quick response and simplification of the device as well as enhanced reliability and lower cost. Also, compensation for $\Delta o + \Delta s$ was heretofore effected by applying to the KDP a high voltage, e.g., several kilovolts, and this in turn involved not only the necessity for electrical parts capable of handling the high voltage but also the need to increase the thickness of the KDP, whereas such disadvantages are eliminated according to the present invention in which only a phase difference of a few degrees is compensated for by the KDP.

I claim:

1. A reflection type ellipsometer for measuring the phase difference of a sample, comprising:
    a source of monochromatic light;
    a polarizer for linearly polarizing light from said light source and passing the linearly polarized light for reflection by the incidence surface of a sample with the azimuth of the polarizer being disposed at an angle of 45° with respect to the incidence surface of the sample;
    an analyser disposed on the path of reflected light from the sample and at an azimuth angle of 45° with respect to the incidence surface of the sample, said angles having opposite signs;
    phase difference compensating means disposed on the light path between said polarizer and said analyser and at an azimuth angle of 0° with respect to said incidence surface for eliminating a predetermined phase difference from polarized light passing therethrough;
    a voltage-responsive double-refractive element on the last-mentioned path for introducing to light passing therethrough a double-refraction phase difference proportional to a control voltage applied thereto;

a photoelectric converter element for photoelectrically converting the analyser output light to an output voltage; and control means responsive to the output voltage from said photoelectric converter element for applying to said double-refractive element a control voltage which causes said double-refractive element to introduce to light passing therethrough a compensating phase difference corresponding to the amount of deviation of the phase difference of said sample from said predetermined phase difference.

2. An ellipsometer according to claim 1, wherein said phase difference compensating means is disposed on the light path between said polarizer and said sample, and said double-refractive element is disposed on the light path between said sample and said analyser.

3. An ellipsometer according to claim 1, wherein said double-refractive element is disposed on the light path between said polarizer and said sample, and said phase difference compensating means is disposed on the light path between said sample and said analyser.

4. An ellipsometer according to claim 1, wherein said phase difference compensating means and said double-refractive element are disposed on the light path between said polarizer and said sample.

5. An ellipsometer according to claim 1, wherein said phase difference compensating means and said double-refractive element are disposed on the light path between said sample and said analyser.

6. An ellipsometer according to claim 1, further comprising means for indicating the value of the voltage applied to said double-refractive element by said control means.

7. An ellipsometer comprising:

means for providing polarized monochromatic light to be intercepted by a sample;

an analyser disposed on the path of light intercepted by the sample;

phase difference compensating means disposed on the light path between said providing means and said analyser for eliminating a predetermined phase difference from polarized light passing therethrough;

electrically controlled compensation means disposed on the last-mentioned light path for introducing to light on that path an adjustable compensating phase difference; and means responsive to light passing from said analyser for electrically controlling the last-mentioned means to cause the adjustable phase difference to correspond to the amount of deviation of the phase difference of the light intercepted by the sample from said predetermined phase difference.

* * * * *